United States Patent
Ng

(10) Patent No.: US 7,618,176 B2
(45) Date of Patent: Nov. 17, 2009

(54) SOLID STATE LIGHT SOURCE ADAPTED FOR REMOTE ILLUMINATION

(75) Inventor: Kee Yean Ng, Penang (MY)

(73) Assignee: Avago Technologies General IP (Singapore) Pte. Ltd., Singapore (SG)

( * ) Notice: Subject to any disclaimer, the term of this patent is extended or adjusted under 35 U.S.C. 154(b) by 148 days.

(21) Appl. No.: 11/473,950

(22) Filed: Jun. 22, 2006

(65) Prior Publication Data

US 2007/0297190 A1 Dec. 27, 2007

(51) Int. Cl.
*F21V 7/04* (2006.01)

(52) U.S. Cl. .................. 362/558; 362/551; 362/554; 362/555; 362/557; 362/582

(58) Field of Classification Search ............. 362/554, 362/555, 558, 551, 572, 574, 575, 559, 577, 362/582; 606/2, 13–17
See application file for complete search history.

(56) References Cited

U.S. PATENT DOCUMENTS

| 5,536,265 | A  | * | 7/1996  | van den Bergh et al. | 606/2 |
|-----------|----|---|---------|----------------------|-------|
| 5,676,603 | A  | * | 10/1997 | Miller               | 473/220 |
| 6,185,356 | B1 | * | 2/2001  | Parker et al.        | 385/133 |
| 7,284,894 | B2 | * | 10/2007 | Mok et al.           | 362/631 |
| 2003/0218880 | A1 | * | 11/2003 | Brukilacchio       | 362/293 |
| 2004/0066659 | A1 | * | 4/2004  | Mezei et al.       | 362/555 |
| 2006/0279950 | A1 | * | 12/2006 | Hama et al.        | 362/257 |

* cited by examiner

*Primary Examiner*—Sandra L O'Shea
*Assistant Examiner*—Jessica L McMillan

(57) ABSTRACT

A lighting device having a light source, light pipe, and a light-dispensing element is disclosed. The light source emits light at a first wavelength and transmits that light to the light pipe. The light dispensing emitter includes an extended section coupled to the light pipe that emits light along the extended section, the extended section having a side surface through which light exits from the extended section. The extended section can include a medium that is transparent to light of the first wavelength and a plurality of scattering centers, the extended section having a shape such that light that is not scattered by the scattering centers is trapped within the extended section by internal reflection. The extended section can also include a light conversion material that converts light of the first wavelength to light of a second wavelength.

9 Claims, 4 Drawing Sheets

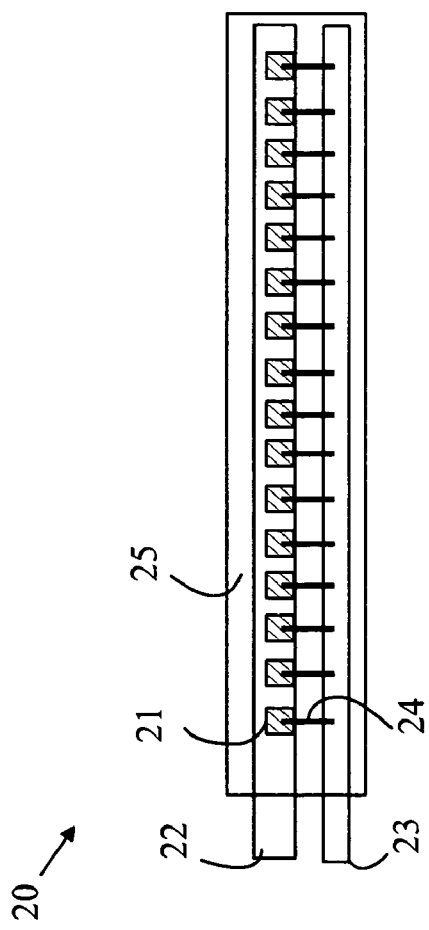
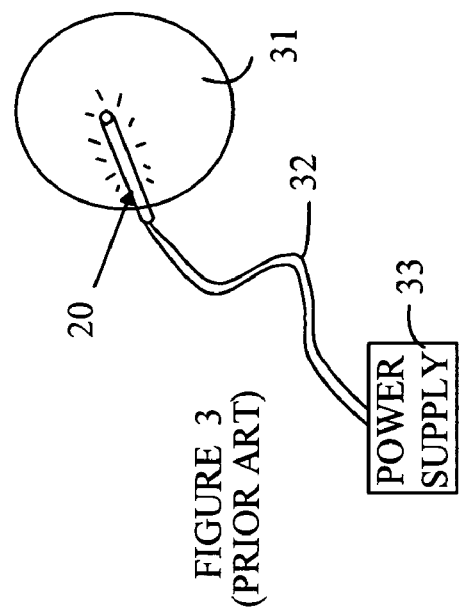
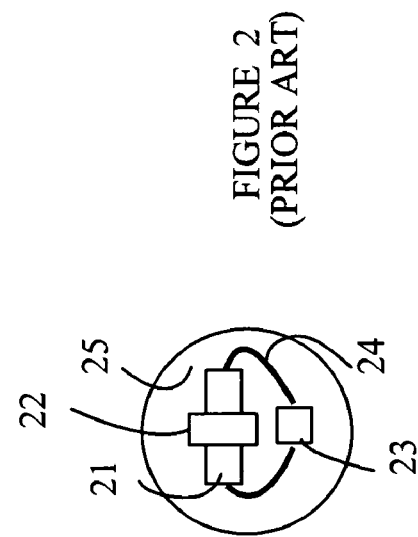
FIGURE 1
(PRIOR ART)
FIGURE 2
(PRIOR ART)
FIGURE 3
(PRIOR ART)

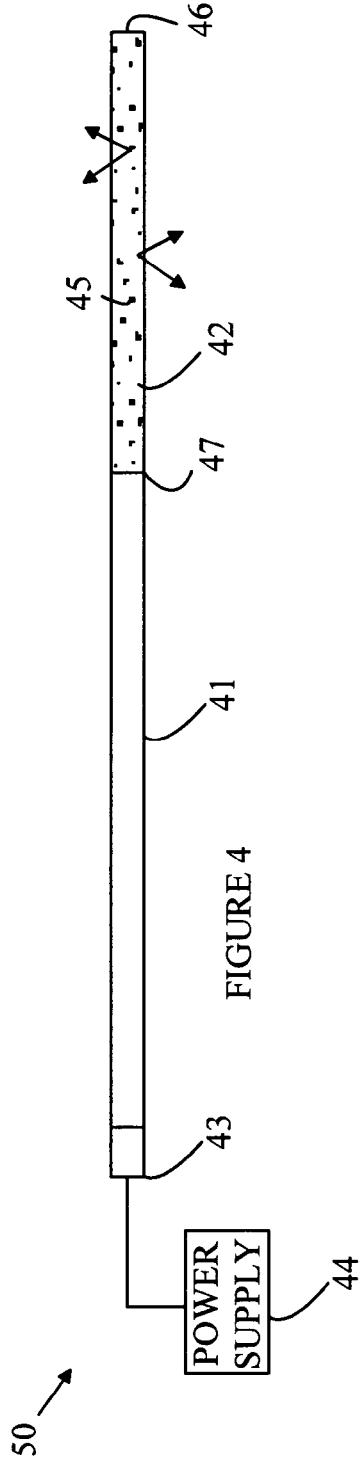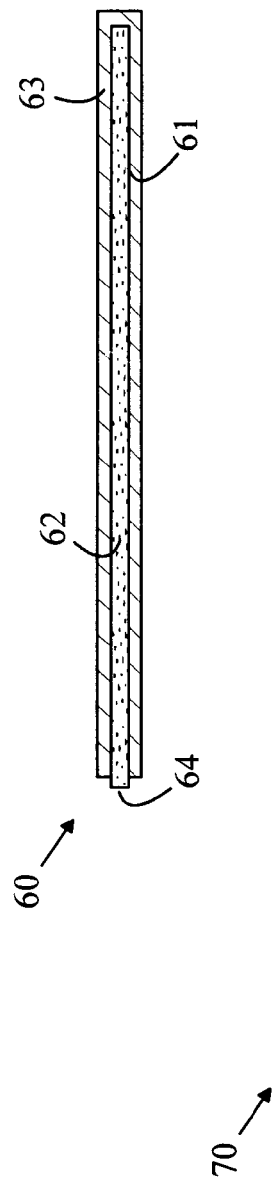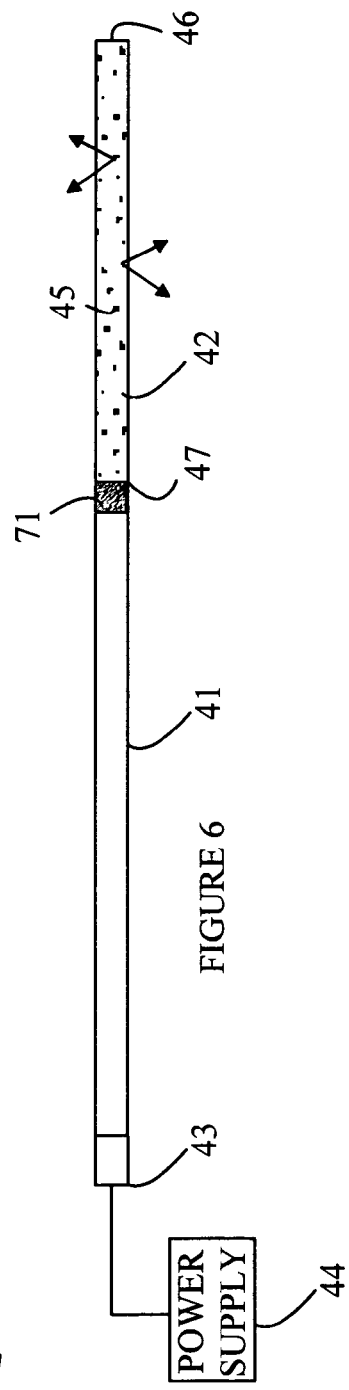

SOLID STATE LIGHT SOURCE ADAPTED FOR REMOTE ILLUMINATION

BACKGROUND OF THE INVENTION

Many potentially useful drugs are too toxic to be administered to a patient at the desired dose. One method for achieving the desired advantages while reducing the overall toxicity of the drug to the patient is referred to as photodynamic therapy (PDT). In PDT, a second drug that will enter the site of interest is administered to the patient. The second drug has three properties. First, the second is less toxic than the drug of interest, and hence, is tolerated better by the patient. The second drug can be converted to the first drug at the site of interest by exposing the second drug to light. Third, the amount of the first drug that escapes the site of interest after conversion of the first drug is less than the toxic limit to which the patient can be exposed once the drug is diluted by diffusing through the patient's body.

Most of the treatment sites of interest are internal to the human body. In addition, the wavelengths of light needed to provide the conversion of the first drug are outside the range of wavelengths that can be delivered through the skin and intervening tissue. Hence, PDT usually requires a light source that can be inserted into the body and placed adjacent to the site of interest.

Solid state light sources are particularly attractive candidates for PDT light sources. Solid state light sources such as LEDs and lasers emit light in narrow wavelength ranges. The particular emission wavelengths are determined by the materials and structure of the solid state devices. The conversion of the first drug to the second drug often displays an optimum range of wavelengths. It should be noted that light that is not consumed in the conversion of the first drug is eventually deposited in the patient's body in the site of interest in the form of heat. Hence, a high conversion efficiency is important to assure that the patient will not be subjected to excess heat.

One class of prior art light source for use in PDT is referred to as a "light bar". The light bar consists of a substrate having a plurality of LEDs attached thereto. The LEDs are encapsulated in a transparent medium. Two electrical leads extend from the light bar and are used to provide power to the device. The light bar is inserted into the patient through a surgically created incision. The leads may or may not be partially within the patient's body.

This arrangement has a number of problems. First, the patient can be subjected to excessive heat. While LEDs have a high conversion efficiency in terms of the conversion of electrical power to light of the desired wavelength relative to conventional light sources such as incandescent bulbs and fluorescent lights, most of the electrical power is still converted to heat. Hence, the light bar can become hot enough to cause discomfort to the patient. To prevent such discomfort, the treatment times must be extended to accommodate the lower intensities of heat, or the concentration of the first drug must be increased. The second option is not always feasible, as the first drug may also have a toxicity problem.

Second, there are lower limits on the size of the light bar. The light bar must be large enough to accommodate the LEDs, substrate, and encapsulating material. The number of LEDs can be relatively large, which leads to a device that requires a correspondingly large incision and the medical problems associated with that incision.

Third, there is a limit to the intensity of light that can be provided by such an arrangement. There is a limit to the density of LEDs mounted on a substrate that is set by the size of the LEDs and the amount of heat that must be removed. Since each LED also has a limit on the amount of light generated, the light bar has a maximum light output per unit area. This limit can place restrictions on the types of drugs that can be activated.

Fourth, the light bar must be sterilized. The encapsulation process can provide a reasonable level of sterilization when the device is first made. However, after the bar has been in a patient, it must be re-sterilized, preferably in an autoclave that subjects the light bar to high temperature steam. This process can lead to delaminating the encapsulation layer or stresses on the internal leads. As a result, light bars are typically discarded after use. As a result, the entire device, including the LEDs and wiring must be replaced, which increases the cost of the procedure.

BRIEF DESCRIPTION OF THE DRAWINGS

FIG. 1 is side view of light bar 20.
FIG. 2 is an end view of light bar 20.
FIG. 3 illustrates light bar 20 inserted into a human body during PDT.
FIG. 4 is a schematic drawing of one embodiment of a light source according to the present invention.
FIG. 5 is a cross-sectional view of a light-dispensing section.
FIG. 6 is a schematic drawing of another embodiment of a light source according to the present invention.

SUMMARY OF THE INVENTION

Figure 7:
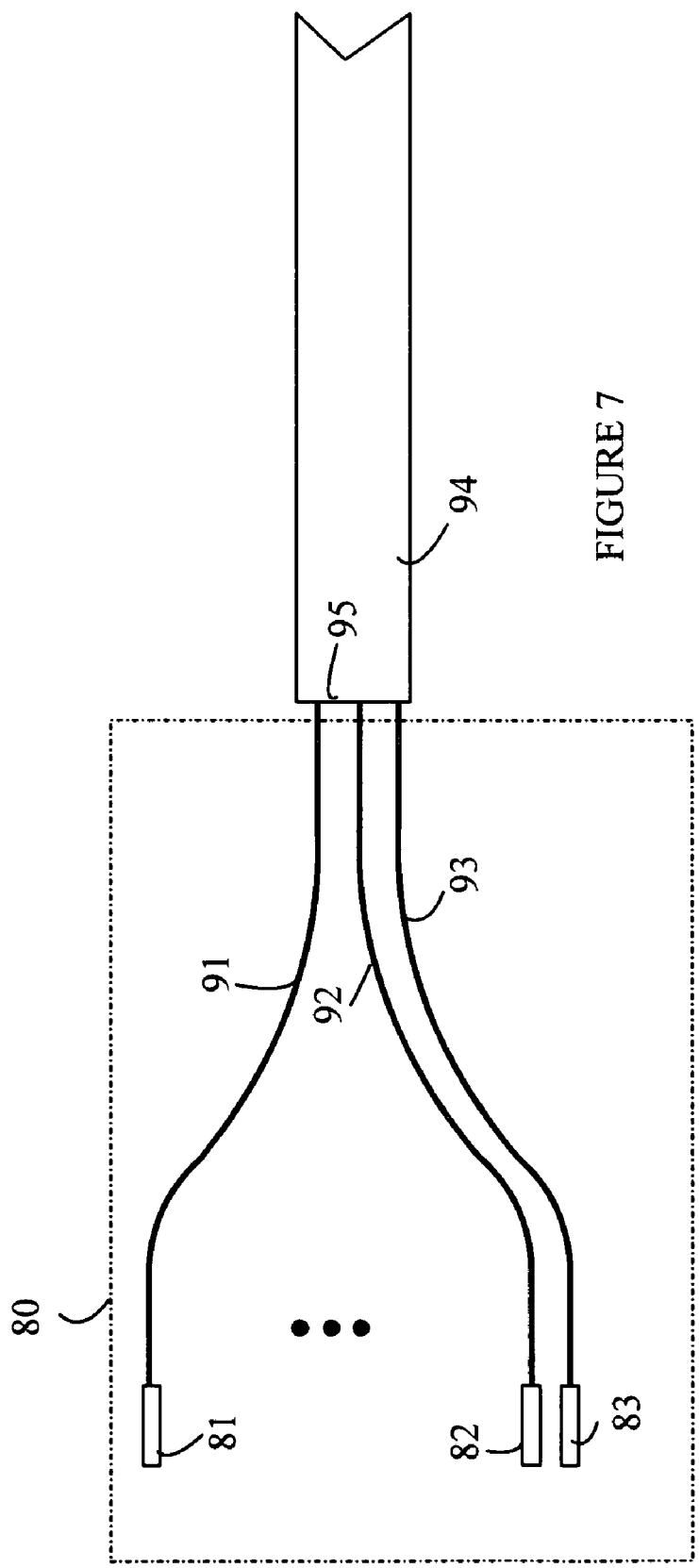
FIG. 7 illustrates a light source 80 connected to a portion of a light pipe that could be used to provide a high level of light to a light-dispensing section.

The present invention includes a lighting device having a light source, light pipe, and a light dispensing element. The light source emits light at a first wavelength and transmits that light to the light pipe. The light dispensing emitter includes an extended section coupled to the light pipe that emits light along the extended section, the extended section having a side surface through which light exits from the extended section. The extended section can include a medium that is transparent to light of the first wavelength and a plurality of scattering centers, the extended section having a shape such that light that is not scattered by the scattering centers is trapped within the extended section by internal reflection.

The extended section can also include a light conversion material that converts light of the first wavelength to light of a second wavelength. The light of the second wavelength is emitted at angles such that the light of the second wavelength leaves the extended section. The light conversion material can include particles of a phosphor or a luminescent material. In addition, the extended section can include a coating that blocks light of the first wavelength from exiting the extended section through the side surface.

In another aspect of the invention, the extended section includes a medium that can be heated to 150 degrees centigrade without deforming so that the extended section can be heat sterilized.

DETAILED DESCRIPTION OF PREFERRED EMBODIMENTS OF THE INVENTION

The manner in which the present invention provides its advantages can be more easily understood with reference to FIGS. 1-3, which illustrate a prior art light bar and the manner in which it is placed in a patient's body during PDT. FIG. 1 is side view of light bar 20, and FIG. 2 is an end view of light bar 20. Light bar 20 is constructed from a plurality of LEDs such as LED 21. Each LED is connected to two conductors 22 and 23. The connections to conductor 22 are made from the bottom of the LED dies, and the connections to conductor 23 are made by wire bonds 24 that connect with a terminal on the top of each LED die. The assembly is encapsulated in a layer of clear medium 25. To provide illumination on both sides of conductor 22, two rows of LEDs are mounted on opposite sides of conductor 22.

Referring to FIG. 3, light bar 20 is inserted into a body 31 during PDT. Light bar 20 is powered by being connected to an external power supply 33 by a pair of wires 32. Since the wires cannot conduct a significant amount of heat from conductor 22, the heat generated by the LEDs is transferred to the patient's body.

Even if the heat dissipation problems do not limit the level of illumination obtained with light bar 20, there is a maximum illumination that is determined by the number of LEDs that can be mounted per unit area on conductor 22. LEDs have a maximum light output per unit area of semiconductor surface at the maximum current allowed through each LED. Hence, once conductor 22 is fully covered with LEDs, no further light output can be achieved. If this level of illumination is insufficient, the treatment time must be extended. Such extended treatment times are costly and subject the patient to added discomfort and risk.

As noted above, light bars are typically used once and then discarded. The encapsulation material through which the wire bonds pass expands and contracts during heat sterilization. This movement stresses the wire bonds and can lead to device failure after relatively few cycles. In addition, the LED dies are bonded to conductor 22 by an epoxy bond that is also weakened by the temperature cycling. To avoid this type of damage and prevent possible cross-contamination between patients, the devices are typically discarded after one use.

The present invention avoids these problems by separating the light generation function from the light delivery function. Refer now to FIG. 4, which is a schematic drawing of one embodiment of a light source according to the present invention. Light source 50 includes three sections. The first section includes a semiconductor light source 43 that is powered by power supply 44. Light source 43 remains outside the patient's body, and hence, heat generated by the light source is not coupled to the patient.

The light from light source 43 is injected into flexible light pipe 41, which couples that light to a light-dispensing section 42 that is placed inside the patient's body at the desired location. Light pipe 41 can be implemented from an optical fiber or a clear tube in which the light is trapped within the light pipe by internal reflection or by reflection from a reflective surface coating. Light-dispensing section 42 can be constructed from a transparent medium that is heat resistant, and hence, can be easily sterilized. For example, section 42 can be constructed from a plastic such as polycarbonate or glass, both of which being capable of withstanding 150 degrees Centigrade.

Light-dispensing section 42 includes a number of scattering centers 45 that scatter the light entering section 42 such that a portion of the scattered light strikes the surface at an angle greater than the critical angle, and hence, exits section 42 and enters the patient's body. In one embodiment of the present invention, the scattering centers can be implemented by dispensing particulate matter in the material from which section 42 is constructed.

In another embodiment, the scattering centers are implemented by forming "pits" in the surface of section 42. The pits can be implemented by providing corresponding features in the mold used to form section 42 or by treating the surface of section 42 after it has been molded. For example, if section 42 is constructed from glass, the surface can be chemically etched or damaged using sand blasting.

It should be noted that the pattern of pits can be controlled in embodiments in which section 42 is etched. The amount of light that exits section 42 at a particular point depends on the amount of light at the location and the density of scattering centers. The density of scattering centers is preferably high enough to guarantee that most of the light exits section 42. If end 46 of section 42 is silvered, the density of scattering centers must be such that the light intensity decreases to less than half by the time the light traverses section 42, is reflected from end 46 and again reaches end 47. Hence, the light intensity along the length of section 42 decreases noticeably, and, as a result, the intensity of light leaving section 42 will be non-uniform if a uniform distribution of scattering centers is utilized. However, if the density of scattering centers increases with distance from end 47, a more uniform illumination pattern is obtained.

As noted above, the wavelength of light that is delivered to the patient's body is preferably matched to the drug being activated by the illumination. The ideal output spectrum for section 42 may differ significantly from that produced by light source 43. This problem can be remedied by utilizing a light source that emits light in a spectral band that has shorter wavelengths than that needed for the therapy and then converting the short wavelength light to the desired wavelength range using a phosphor or luminescent material.

Refer now to FIG. 5, which is a cross-sectional view of a light-dispensing section 60 that utilizes phosphor particles to convert the light from the wavelength band generated by the light source to light in a therapeutic band needed to activate a particular drug. Light having a wavelength that is shorter than the wavelengths in the therapeutic band is introduced into light-dispensing section 60 at end 64. Light-dispensing section 60 includes a transparent rod 61 that has particles 62 of a phosphor that will convert light of the input wavelength to light in the desired band. Since the phosphor particles emit the converted light in all directions, the particles also serve the function of the scattering centers discussed above.

If the input light is of a wavelength that would be detrimental to the patient. e.g., UV light, the outer surface of light-dispensing section 60 can be covered with a layer 63 that blocks that light while allowing light of the desired wavelengths to exit. A dichroic reflector is particularly useful for layer 63, since such a reflector reflects any escaping input light back into the material in which the phosphor particles are located, and hence, increases the conversion efficiency of light-dispensing section 60. Alternatively, layer 63 can be a band pass filter that absorbs light of the input light wavelength.

In another embodiment, transparent rod 61 includes a soluble phosphor material. In such embodiments, the losses associated with scattering of the input light from the phosphor particles due to the difference in index of refraction between the transparent material and the phosphor material are eliminated. In this case, the individual phosphor molecules can be viewed as the "scattering centers". Accordingly, the term scattering center is defined to include redirection of light by a phosphor molecule that converts the light to a different wavelength prior to emitting the output light in a uniform angular distribution.

In the above-described embodiments, the light from the light source was converted to the therapeutic wavelength in the light-dispensing section. However, embodiments in which the light converting material resides in a layer in light pipe 41 can also be constructed. Refer now to FIG. 6, which is a schematic drawing of another embodiment of a light source according to the present invention. To simplify the following discussion, those elements of light source 70 that serve functions analogous to those described above with respect to light source 50 have been given the same numeric designations and will not be discussed further here. Light source 70 includes a layer 71 that converts light of the wavelength generated by light source 43 to light in the desired band of wavelengths. Layer 71 can include phosphor or luminescent particles or soluble materials as described above. Since the light converting materials emit light in all directions, layer 71 is preferably close to end 47 to reduce the amount of light that is lost.

In one embodiment, layer 71 is included in a removable coupler that couples light pipe 41 to light-dispensing section 42. In this embodiment, the therapeutic emission band can be altered merely by changing the coupler, as opposed to replacing the entire light-dispensing section. However, as noted above, this type of system has increased light losses, and hence, requires a more intense light source. It should also be noted that light-dispensing section 42 may include an outer filter or a dichroic filter to prevent unconverted light that enters light-dispensing section 42 from reaching the patient.

Light source 43 can be constructed from any suitable light source that can inject light efficiently into light pipe 41. Since the light pipe is remote from the patient, considerations of size and heat dissipation are of less concern than in the case of the prior art light bar discussed above.

In one embodiment of the present invention, light source 43 is constructed from one or more semiconductor lasers. Since lasers emit light in a collimated beam, coupling the light into a small fiber is more easily accomplished than with an LED. Refer now to FIG. 7, which illustrates a light source 80 connected to a portion of a light pipe 94 that could be used to provide a high level of light to a light-dispensing section. Light source 80 utilizes a plurality of laser diodes. Exemplary laser diodes are shown at 81-83. The light from each laser diode is coupled into a corresponding optical fiber. The optical fibers corresponding to laser diodes 81-83 are shown at 91-93, respectively. One end of each optical fiber is bonded to surface 95 of light pipe 94. Since the light from the laser diodes is collimated, a simple lens can be used to focus the light to a small point on the surface of each optical fiber, and hence, very small diameter optical fibers can be utilized, and the outputs of a large number of laser diodes can be coupled to light pipe 94 to create an intense light source that is delivered to the light-dispensing section.

While laser diodes provide a more intense light source, the cost of such a light source is significantly greater than a light source of a similar construction that utilizes LEDs. Since the LEDs emit light into a large cone of angles from a source that has a finite area, the coupling between the LEDs and the optical fibers requires that the LEDs be placed a significant distance from the imaging lens used to perform the coupling. Alternatively, larger diameter optical fibers can be utilized.

Figure 8:
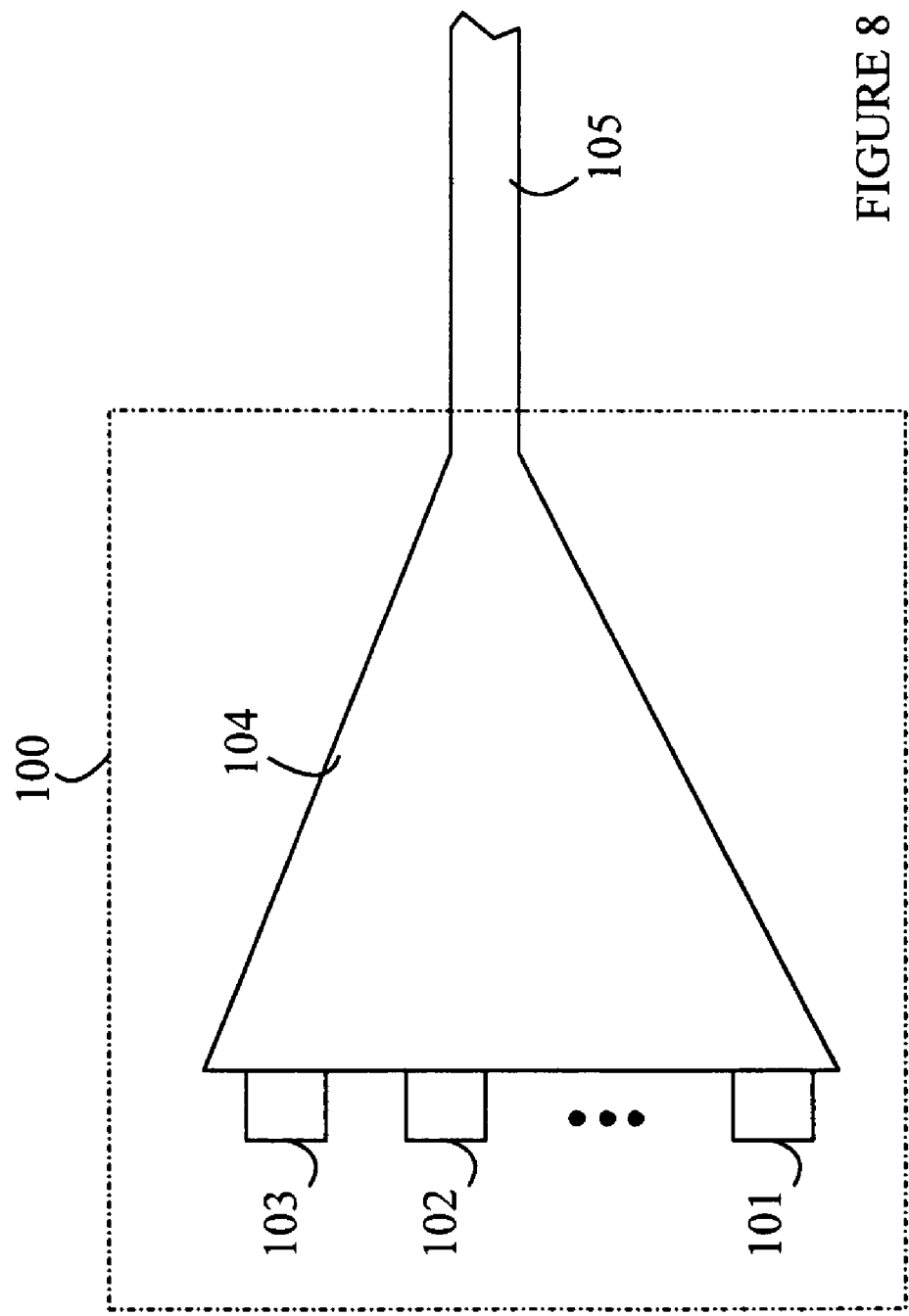
FIG. 8 illustrates another embodiment of a light source for use with the present invention.

The arrangement shown in FIG. 7 couples light from an extended light source into a light pipe that has a smaller diameter than the dimensions of the light source. In the case of light source 80, the coupling is accomplished with a number of optical fibers. However, other optical coupling arrangements can be utilized. Refer now to FIG. 8, which illustrates another embodiment of a light source for use with the present invention. Light source 100 includes a plurality of LEDs that are coupled to the face of a first light pipe 104. Exemplary LEDs are shown at 101-103. Light pipe 104 has a truncated conical shape that directs the light from the various LEDs into light pipe 105, which, in turn, delivers the light to a light-dispensing section as described above.

The light pipe that connects the light source to the light-dispensing section can be constructed from either flexible or solid materials. Flexible materials provide a more easily manipulated therapeutic system; however, a device with a rigid light pipe can still be utilized. If the light pipe is flexible, a reflective coating can be provided on the outside surface to reduce light losses from light that strikes the surface at angles greater than the critical angle when the light pipe is bent. As noted above, the light pipe section can also be constructed from optical fibers. A bundle of optical fibers could be used to replace light pipe 94 discussed above. In this case, the individual fibers from the semiconductor light sources can be bundled together and used for the light pipe that is connected to the face of the light-dispensing section. Alternatively, a flexible light-dispensing section constructed from medical grade silicone can be utilized to provide a light-dispensing section that has a wide range of flexibility determined by the specific silicone composition.

The above-described embodiments of the present invention have been directed to systems for use in PDT. However, embodiments intended for other applications can also be constructed. For example, a light source according to the present invention could be utilized in endoscopic surgery or to provide illumination in environments in which a thin light source is needed to reach an inaccessible location. In addition, it should be noted that the light-dispensing section does not contain any power source, and hence, can safely be introduced into environments having a combustible atmosphere, provided the power supply remains outside the environment in question.

Various modifications to the present invention will become apparent to those skilled in the art from the foregoing description and accompanying drawings. Accordingly, the present invention is to be limited solely by the scope of the following claims.

What is claimed is:

1. An apparatus comprising:
   a light source that emits light at a first wavelength;
   a light pipe that receives said light of said first wavelength; and
   a light dispensing emitter comprising an extended section coupled to said light pipe that emits light along said extended section, said extended section having a side surface through which light exits from said extended section;
   wherein said extended section comprises a medium that is transparent to light of said first wavelength and a plurality of scattering centers, said extended section having a shape such that light that is not scattered by said scattering centers is trapped therein by internal reflection.

2. The apparatus of claim 1 wherein said extended section comprises a light conversion material that converts light of said first wavelength to light of a second wavelength, light of said second wavelength being emitted at angles such that said light of said second wavelength leaves said extended section.

3. The apparatus of claim 2 wherein said light conversion material comprises particles of a phosphor or luminescent material.

4. The apparatus of claim 2 wherein said extended section comprises a coating that reflects light of said first wavelength from said side surface.

5. The apparatus of claim 1 wherein said extended section comprises a medium that can be heated to 150 degrees centigrade without deforming.

6. The apparatus of claim 1 wherein said light source comprises a plurality of semiconductor light sources and an optical system for combining light therefrom and introducing that combined light into said light pipe.

7. The apparatus of claim 1 wherein said light pipe is flexible.

8. The apparatus of claim 1 wherein said scattering centers are uniformly distributed throughout the extended section.

9. The apparatus of claim 1 wherein density of scattering centers increases with distance starting at the location that light enters the extended section and ending where the extended section ends.

* * * * *